United States Patent [19]
Roe et al.

[11] Patent Number: 4,820,819
[45] Date of Patent: Apr. 11, 1989

[54] 5-PHENYL-3[2H]-PYRIDAZINONE DERIVATIVES

[75] Inventors: Anthony M. Roe, Hatfield; William J. Coates, Welwyn Garden City; Robert A. Slater, Letchworth; Stephen P. Breukelman, Bristol; George D. Meakins, Oxford, all of England

[73] Assignee: Smith Kline & French Laboratories Limited, Welwyn Garden City, United Kingdom

[21] Appl. No.: 28,375

[22] Filed: Mar. 20, 1987

Related U.S. Application Data

[60] Division of Ser. No. 896,498, Aug. 13, 1986, Pat. No. 4,678,786, which is a continuation of Ser. No. 642,979, Aug. 21, 1984, abandoned.

[30] Foreign Application Priority Data

Sep. 2, 1983 [GB] United Kingdom ................ 8323553

[51] Int. Cl.$^4$ ................ C07D 237/04; C07D 237/14; A61K 31/50

[52] U.S. Cl. .................................................. 544/239
[58] Field of Search ................ 544/235, 239; 514/247

[56] References Cited

U.S. PATENT DOCUMENTS

| | | | |
|---|---|---|---|
| 3,931,177 | 1/1976 | Coates et al. | 544/239 |
| 4,053,601 | 10/1977 | Coates et al. | 514/247 |
| 4,397,854 | 8/1983 | Sircar | 424/250 |
| 4,508,721 | 4/1985 | Hargreaves | 514/252 |
| 4,521,416 | 6/1985 | Sircar et al. | 514/252 |

OTHER PUBLICATIONS

Bourguignon et al., J. Org. Chem., 1981, 46, 4889–4894.

Primary Examiner—Mark L. Berch
Attorney, Agent, or Firm—Nancy S. Mayer; Stuart R. Suter; Janice E. Williams

[57] ABSTRACT

This invention relates to (isopropyl and tertiary butylamino-2-hydroxypropoxy)phenyl-3[2H]-pyridazinones which have β-adrenoceptor antagonist activity.

10 Claims, No Drawings

5-PHENYL-3[2H]-PYRIDAZINONE DERIVATIVES

This is a division of application Ser. No. 896,498 filed Aug. 13, 1986 now U.S. Pat. No. 4,078,786 which is a continuation of Ser. No. 642,979 filed Aug. 21, 1984 now abandoned.

The present invention relates to pharmaceutical compositions containing pyridazinone derivatives for use as β-adrenoceptor antagonists, and in particular to such compositions wherein the pyridazinone is substituted by a phenyl group substituted by a β-blocking side chain. This invention also relates to methods of producing β-adrenoceptor antagonist activity with these pyridazinone derivatives and to certain novel compounds which may be used in the compositions and methods of this invention.

Pyridazinones substituted in the 6-position by a phenyl group having a β-blocking side-chain are generically known from U.S. Pat. No. 4,053,601. However they are described therein as intermediates in the preparation of hydrazine derivatives which are stated to have β-adrenoceptor antagonist and vasodilator activity. There is no suggestion that the intermediates would have any useful pharmacological activity.

Accordingly the present invention provides a compound of the formula (I):

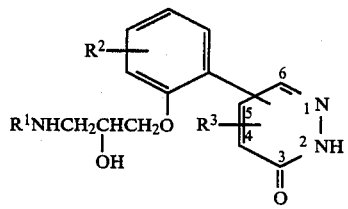

or a pharmaceutically acceptable salt thereof, wherein
$R^1$ is isopropyl or tertiary-butyl;
$R^2$ is hydrogen, $C_{1-4}$alkyl, $C_{1-4}$alkoxy, hydroxy or amino; and
$R^3$ is hydrogen or methyl; for use as a β-blocker.

Suitably $R^1$ is an isopropyl group. Preferably $R^1$ is a tertiary-butyl group.

$R^2$ is hydrogen, $C_{1-4}$alkyl for example methyl or ethyl, $C_{1-4}$alkoxy for example methoxy or ethoxy, amino or hydroxy.

Suitably $R^2$ is hydrogen, amino or methyl. Preferably $R^2$ is hydrogen.

When $R^2$ is not hydrogen it is preferably in a meta- or para-position to the pyridazinone ring.

Favourably the phenyl group is substituted in the 5- or 6-position of the pyridazinone ring, preferably in the 5-position.

Thus preferred compounds for use in this invention are those of the formula (II):

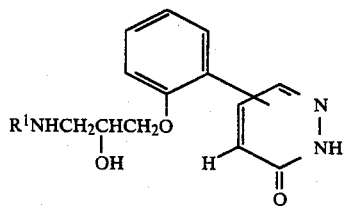

and pharmaceutically acceptable salts thereof wherein $R^1$ is as hereinbefore defined.

Particular compounds for use in this invention are:
5-[2-(3-t-butylamino-2-hydroxypropoxy)phenyl]-3[2H]-pyridazinone and pharmaceutically acceptable salts thereof,
5-[2-(2-hydroxy-3-isopropylaminopropoxy)phenyl]-3[2H]-pyridazinone and pharmaceutically acceptable salts thereof,
6-[4-amino-2-(3-t-butylamino-2-hydroxypropoxy)-phenyl]-3[2H]-pyridazinone and pharmaceutically acceptable salts thereof,
6-[2-(3-t-butylamino-2-hydroxypropoxy)phenyl]-3[2H]-pyridazinone and pharmaceutically acceptable salts thereof,
4-[2-(3-t-butylamino-2-hydroxypropoxy)phenyl]-3[2H]-pyridazinone and pharmaceutically acceptable salts thereof,
6-[2-(2-hydroxy-3-isopropylaminopropoxy)phenyl]-3[2H]-pyridazinone and pharmaceutically acceptable salts thereof,
6-[2-(3-t-butylamino-2-hydroxypropoxy)-4-methoxyphenyl]-3[2H]-pyridazinone and pharmaceutically acceptable salts thereof, and
5-methyl-6-[2-(3-t-butylamino-2-hydroxypropoxy)-phenyl]-3[2H]-pyridazinone and pharmaceutically acceptable salts thereof.

The compounds for use in this invention have a chiral centre at the —CH(OH)— moiety in the side chain. Suitably they are provided as a racemic mixture or a mixture of the R- and S-isomers in which the proportion of S-isomer is enhanced. Preferably the compounds for use in this invention are provided as a racemic mixture or as the S-isomer substantially free of the R-isomer, for example having less than 10% R-isomer, more suitably less than 5% and preferably less than 2%.

The compounds of the formulae (I) and (II) may form pharmaceutically acceptable acid addition salts with either organic or inorganic acids, for example those formed with hydrochloric, hydrobromic, hydriodic, methanesulphonic, sulphuric, maleic, fumaric, succinic, acetic, tartaric, citric and lactic acids.

In another aspect the present invention provides a pharmaceutical composition which comprises a compound of the formula (I) or a pharmaceutically acceptable salt thereof and a pharmaceutically acceptable carrier.

The compositions of this invention include those in a form adapted for oral, rectal, ocular or parenteral use, and may be used for the treatment of humans and other mammals. Thus, the compounds of the formula (I) and pharmaceutically acceptable salts thereof may be administered, for example, orally, rectally, ocularly or parentally.

In a preferred composition aspect of this invention a compound of the formula (I) or pharmaceutically acceptable salt thereof is in sterile form.

Suitably the compounds of the formula (I) and their pharmaceutically acceptable salts may be formulated as solutions, suspensions, syrups, capsules, lozenges, reconstitutable powders, tablets and sterile forms suitable for injection or infusion. These compositions may contain conventional pharmaceutically acceptable materials such as diluents, binders, flavours, preservatives, disintegrants and colouring agents. Suitable examples of solid carriers include lactose, sucrose, talc, gelatin, agar, starch, magnesium stearate and acacia. Suitable examples of liquid carriers include polyvinylpyrrolidine, lecithin, polyethyleneglycol, arachis oil, syrup, glycerine, water, ethanol, peanut oil and olive oil.

A typical suppository formulation comprises a compound of formula (I) or a pharmaceutically acceptable salt thereof which is active when administered in this way, with a binding and/or lubricating agent for example gelatin or cocoa-butter or other low melting vegetable waxes or fats.

Typical ophthalmic formulations comprise a compound of the formula (I) or a pharmaceutically acceptable salt thereof, which is active when administered in this way, in the form of an ointment, a solid for example a solid insert suitably having a solid water-soluble polymer as carrier, or a buffered isotonic liquid for example phosphate buffer, isotonic sodium borate, isotonic boric acid or isotonic sodium chloride.

Preferably the composition is in unit dosage form for example a tablet or capsule.

Each dosage unit contains preferably from about 10 to 500 mg of a compound of formula (I) or a pharmaceutically acceptable salt thereof calculated as the free base, preferably from about 25 mg to about 250 mg.

The invention also provides a method of producing β-adrenoceptor antagonist activity which comprises administering to a subject an effective amount to produce said activity of a compound of the formula (I) or a pharmaceutically acceptable salt thereof.

The daily dosage regimen for an adult patient is from about 10 mg to about 1500 mg of the compound of formula (I) or a pharmaceutically acceptable salt thereof calculated as the free base. The active ingredient may be administered from 1 to 6 times a day, sufficient to effect β-adrenergic blockade. For ocular administration suitably 0.01 to 30 mg of the compound of the formula (I) or pharmaceutically acceptable salt thereof (calculated as the free base) is administered daily, in 1 to 6 doses. Suitable concentrations for the active compound in the carrier are 0.01 to 25% dependent on the nature of the carrier; typical concentrations for eye drop solutions are 0.25–0.5% suitably containing 1–5 mg of active compound.

The compounds of the formula (I) are β-adrenoceptor antagonists and can be used in the treatment of any disease that is conventionally treated with such drugs, for example angina, myocardial infarction, hypertension, arrhythmias, thyrotoxicosis, anxiety, migraine and tremor. The compounds of the formula (I) are also useful for treating glaucoma and lowering intraocular pressure. The β-adrenoceptor antagonist activity of the compounds of the present invention may be demonstrated in a suitable test preparation such as cats anaesthetised with pentobarbitone sodium (Nembutal, Trade Mark), 60 mg/kg i.p. In such anaesthetised cats, intravenous injections of isoprenaline cause tachycardia, and vasodilatation in the hindlimb. These effects of isoprenaline, which are dose-dependent and are due to stimulation of β-adrenoceptors, can be reduced or abolished by intravenous administration of from about 0.01 to 100 micromoles/kg of the β-adrenoceptor antagonist of formula (I). The compounds of Examples 1 to 7 were administered to anaesthetised cats and the doses (μmol/Kg intravenous) required to cause 50% reduction (ED$_{50}$) in isoprenaline-induced tachycardia ($\beta_1$) and 50% reduction in isoprenaline-induced vasodilatation ($\beta_2$) were recorded. The compounds of the Examples 2–7 gave ED$_{50}$ values in the range of 0.04 to about 0.5 ($\beta_1$) and 0.01 to 0.25 ($\beta_2$). The compound of Example 1 gave ED$_{50}$ values below 0.01 for both $\beta_1$ and $\beta_2$ tests.

In a further aspect of this invention there are provided novel compounds within the formula (I) which are represented by the formula (III):

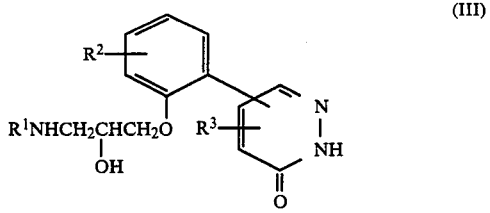

(III)

and pharmaceutically acceptable salts thereof wherein R$^1$ and R$^2$ are as hereinbefore defined with the proviso that when the pyridazinone is 6-substituted the S-isomer is provided. Suitable and favourable substituents for the novel compounds of this invention are as previously described for the compounds for use as β-adrenoceptor antagonists. By S-isomer we mean the S-isomer substantially free of the R-isomer, for example having less than 10% R-isomer, more suitably less than 5% and preferably less than 2%.

Thus particularly preferred compounds of this invention are:

5-[2-(3-butylamino-2-hydroxypropoxy)phenyl]-3[2H]-pyridazinone and pharmaceutically acceptable salts thereof and 5-[2-(2-hydroxy-3-isopropylamino-propoxy)phenyl]-3[2H]-pyridazinone and pharmaceutically acceptable salts thereof.

In another aspect the present invention provides a process for the preparation of a compound of the formula (III) or a pharmaceutically acceptable salt thereof, which process comprises:

(a) for 4- and 5-phenyl pyridazinones, the reaction of a compound of the formula (IV):

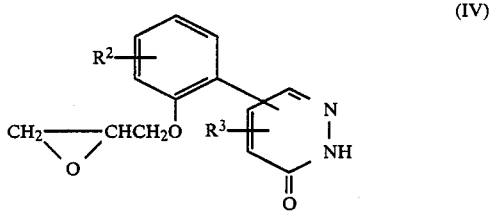

(IV)

wherein R$^2$ and R$^3$ are as hereinbefore defined, with isopropylamine or tertiary butylamine; or (b) the reaction of a compound of the formula (V):

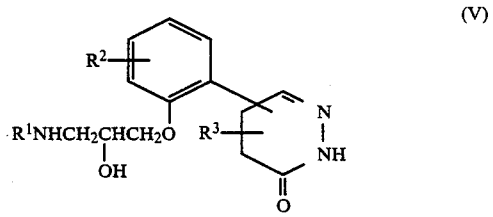

(V)

wherein R$^1$, R$^2$ and R$^3$ are as hereinbefore defined, with a dehydrogenating agent; or (c) the hydrolysis of a compound of the formula (VI):

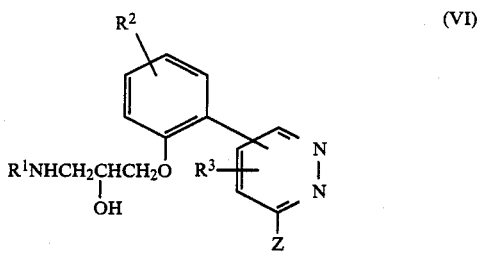

(VI)

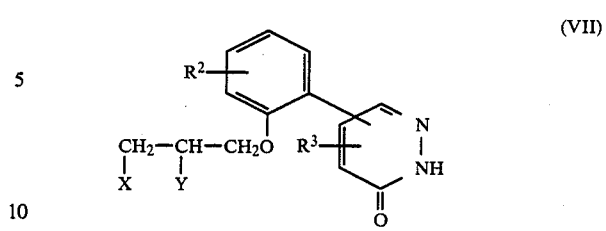

(VII)

wherein $R^1$, $R^2$ and $R^3$ are as hereinbefore defined, and Z is $C_{1-6}$alkoxy, allyloxy, optionally substituted benzyloxy, or halo; or (d) the resolution of a compound of the formula (III) when in racemic form to provide the S-isomer; and if necessary forming a pharmaceutically acceptable salt.

The reaction of a compound of the formula (IV) and either isopropylamine or tertiary-butylamine is suitably conducted in a solvent at an elevated temperature, for example, in refluxing toluene.

Suitable dehydrogenating agents for reaction with a compound of the formula (V) include oxidative halogenating agents for example chloranil or sodium 3-nitrobenzenesulphonate. In addition N-bromosuccinimide is suitable for converting a compound of the formula (V) to a compound of the formula (I) when the phenyl ring is substituted at the 4- or 5-position of the pyridazinone ring. The conditions for such reactions will vary according to the reagent used, but will be conventional, for example N-bromosuccinimide may be used in a solvent, for example dimethylsulphoxide, at a non-extreme temperature, for example ambient.

Suitably in the compounds of the formula (VI) Z is $C_{1-6}$alkoxy for example methoxy or ethoxy. The dealkylation is conveniently performed by acidic hydrolysis. Alternatively Z suitably may be halo for example chloro which is subjected to acidic hydrolysis.

Racemic mixtures of the compounds of the formula (III) may be resolved by conventional methods.

During the processes of this invention the side chain may be protected on the amino and/or hydroxy group if desired. For example the hydroxy group may be acylated for example as $CH_3COO-$ which may be removed by basic hydrolysis.

Pharmaceutically acceptable salts of the compounds of the formula (III) may be prepared in conventional manner, for example acid addition salts may be prepared by treating the compounds of the formula (III) with the appropriate acid in a $C_{1-4}$alkanol, or they may be prepared by the use of an ion-exchange resin to form the desired salt directly from the free base or via a different acid addition salt.

The compounds of the formula (IV) may be formed by the reaction of base with a compound of the formula (VII):

wherein $R^2$ and $R^3$ are as hereinbefore defined, and one of X and Y is halo for example bromo and the other is hydroxy. Suitably the base is t-butylamine or isopropylamine, in which case the compound of the formula (IV) is suitably an unisolated intermediate in the preparation of a compound of the formula (III).

The compounds of the formula (VII) may be conveniently prepared by the reaction of a compound of the formula (VIII):

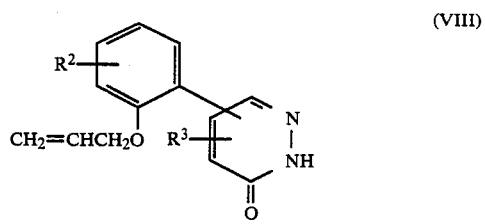

(VIII)

wherein $R^2$ and $R^3$ are as hereinbefore defined, with an oxidative halogenating agent, for example N-bromosuccinimide.

The compounds of the formula (VIII) may be prepared by the dehydrogenation of a compound of the formula (IX):

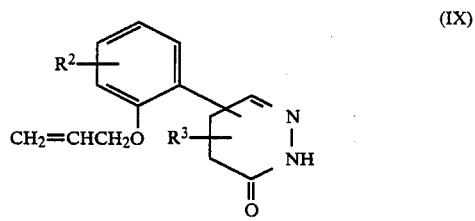

(IX)

wherein $R^2$ and $R^3$ are as hereinbefore described, in a manner analogous to that described for dehydrogenation previously.

In a particularly convenient aspect a compound of the formula (IX) may be reacted with an oxidative halogenating agent, for example N-bromosuccinimide, to provide the compound of the formula (VII) without isolation of the intermediate.

Alternatively the compound of the formula (IV) may be prepared by the alkylation of a compound of the formula (X):

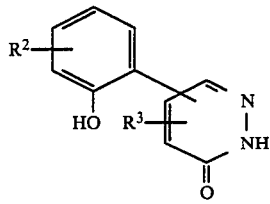
(X)

wherein R² and R³ are as hereinbefore defined, with an alkylating agent, for example epichlorohydrin or epibromohydrin.

The compounds of the formula (X) may be prepared by the dehydrogenation of a compound of the formula (XI):

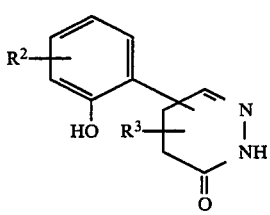
(XI)

wherein R² and R³ are as hereinbefore defined, in a manner analogous to that described for dehydrogenation previously.

The compounds of the formulae (V) and (VI) may be prepared by elaborating an hydroxy group to R¹NHCH₂CH(OH)CH₂O— by the same general manner as hereinbefore described. Thus compounds of the formulae (IX) and (V) may be prepared from compounds of the formula (XI) and compounds of the formula (VI) may be prepared from the compounds of the formula (XII):

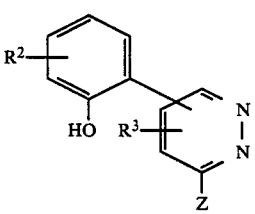
(XII)

wherein R², R³ and Z are as hereinbefore defined.

The compounds of the formulae (XI) and (XII) and also compounds of the formulae (IV)–(X), wherein the phenyl ring is substituted at the 6-position of the pyridazinone ring, may be prepared for example by methods described in the U.S. Pat. Nos. 3,931,177 and 4,053,601.

Compounds of the formulae (IX), (X) and (XI) wherein the phenyl ring is substituted at the 4- or 5-position of the pyridazinone ring may be prepared in the same general manner as for the 6-substituted compounds. For example by reacting with hydrazine an appropriately substituted 2- or 3-phenyl ω-carboxypropionaldehyde wherein the aldehyde and acid functions are "masked" if necessary, for example the aldehyde function may be in the form of an acetal or the aldehyde and acid functions may be joined to form a hydroxy- or alkoxy-lactone, to form a dihydropyridazinone ring. The β-blocking side chain then may be elaborated and dehydrogenated as necessary. In addition 5-phenyldihydropyridazinones may be prepared by reacting a 4-phenylfuran-2-one with hydrazine. See also, for example, the methods of Bourguignon and Wermuth, J. Org. Chem. 1981, 4889–4894 for the preparation of 5-phenylpyridazinones.

Furthermore compounds of the formula (XII) wherein the phenyl ring is substituted at the 4-position of the pyridazinone ring, may be prepared by known methods. For example compounds wherein Z is chloro may be prepared by reaction of phosphorus oxychloride with a corresponding compound of the formula (X) wherein the hydroxy group is protected. Such compounds of the formula (X) may be prepared by a Grignard reaction with 4-chloropyridazinone and a protected hydroxyphenyl magnesium bromide. Compounds of the formula (XII) wherein Z is alkoxy may be prepared by the methods of Example 3 with appropriate protection of the R² substituent if necessary.

As previously stated racemic mixtures of the compounds of the formula (III) may be resolved by conventional methods. Alternatively any resolution may be performed on intermediates as described hereinbefore at any convenient stage of the synthesis.

The following Examples serve to illustrate the invention.

EXAMPLE 1

5-[2-(3-t-Butylamino-2-hydroxypropoxy)phenyl]-3[2H]-pyridazinone hydrochloride (i) 4-(2-Allyloxyphenyl)-5-ethoxydihydro-2-furanone Potassium hydroxide (8.5 g) in methanol (60 ml) was added to a solution of ethyl coumarin-3-carboxylate (10 g) in methanol (100 ml) and the mixture was refluxed for 90 minutes, whereupon a precipitate formed. Allyl bromide (18 ml) in methanol (20 ml) was added, the precipitate dissolved, the mixture was refluxed for a further two hours whereupon another precipitate formed. The mixture was poured into water and extracted into diethyl ether. The ether extracts were washed with aqueous sodium hydroxide, water, dried over MgSO₄ and then evaporated under reduced pressure to give as an oil a mixture of allyl and methyl esters of 2-allyloxybenzylidenemalonic acid (7 g). This was combined with material obtained from a larger scale reaction.

A solution of the foregoing esters (23 g) in tetrahydrofuran (25 ml) was added to methyl methylsulphinylmethylsulphide (8.5 ml) and butyl lithium (6 g) in tetrahydrofuran (100 ml) and hexane (60 ml) at −70° C. The resultant solution was warmed to room temperature, poured into aqueous ammonium chloride, extracted into diethyl ether and evaporated under reduced pressure to afford slightly impure ethyl 3-(2-allyloxyphenyl)-2-ethoxycarbonyl-4-methylsulphinyl-4-methylthiobutanoate (30.2 g) as a yellow oil. This material was dissolved in a mixture of triethyl orthoformate (18 ml), sulphuric acid (1 ml) and anhydrous ethanol (90 ml). After three days the solution was poured into aqueous sodium bicarbonate, extracted into diethyl ether and evaporated under reduced pressure to afford ethyl 3-(2-allyloxyphenyl)-4,4-diethoxy-2-ethoxycarbonylbutanoate as a brown oil. A solution of this material (26 g) and potassium hydroxide (14 g) in ethanol (140 ml) was refluxed for four hours, poured into water and acidified with concentrated hydrochloric acid to yield, on extraction into diethyl ether and evaporation under reduced pressure, 3-(2-allyloxyphenyl)-2-carboxy-4,4-diethoxybutanoic acid (15.5 g) as a brown oil. This acid (15 g) was distilled (Hg diffusion pump) to give 4-(2-allyloxyphenyl)-5-ethoxydihydro-2-furanone (10.6 g) as a yellow oil, boiling point 200° C. (bath temperature)/less than 0.01 mm Hg.

(ii)
5-(2-Allyloxyphenyl)-4,5-dihydro-3[2H)pyridazinone

Hydrazine hydrate (2.8 ml) was added to a solution of 4-(2-allyloxyphenyl)-5-ethoxydihydro-2-furanone (9.8 g) in acetic acid (30 ml) and water (27 ml). The solution was refluxed for 90 minutes, poured into aqueous sodium bicarbonate, extracted into diethyl ether, evaporated under reduced pressure and the resultant solid recrystallised from benzene to afford 5-(2-allyloxyphenyl)-4,5-dihydro-3[2H]-pyridazinone (6.5 g) as white crystals, m.p. 93°–95° C.

(iii)
5-[2-(3-t-Butylamino-2-hydroxypropoxy)phenyl]-3[2H]-pyridazinone hydrochloride N-Bromosuccinimide (2.2 g) was added to a solution of 5-(2-allyloxyphenyl)-4,5-dihydro-3[2H]-pyridazinone (1.4 g) and water (0.5 ml) in dimethylsulphoxide (20 ml). After three hours the solution was diluted with ethyl acetate, washed with water, dried and evaporated under reduced pressure to yield an oil (2.2 g). This oil was dissolved in t-butylamine (20 ml) and toluene (90 ml) and the solution refluxed for three days. The mixture was poured into dilute sulphuric acid, washed with ether, basified with aqueous sodium hydroxide, extracted into ethyl acetate and evaporated under reduced pressure to afford 5-[2-(3-t-butylamino-2-hydroxypropoxy)phenyl]-3-[2H]-pyridazinone (1.3 g) as an oil.

This was dissolved in 0.1M hydrochloric acid (38 ml), washed with ether and the water removed under reduced pressure to give a solid (1.5 g) which was recrystallised from ethanol-water to give the title compound (1.3 g) as white crystals, m.p. 265°–267° C. (decomp.)

The title compound (25 mg), sucrose (40 mg), starch (15 mg), talc (3 mg) and stearic acid (1 mg) are screened, mixed and filled into a hard gelatin capsule.

EXAMPLE 2

6-[4-Amino-2-(3-t-butylamino-2-hydroxypropoxy)phenyl]-3[2H]-pyridazinone (i) 4-Acetamido-2-hydroxyacetophenone (50 g), anhydrous potassium carbonate (53.8 g) and allyl bromide (24.63 ml) were vigorously stirred and refluxed in anhydrous acetone (200 ml) for 19 hours. Further allyl bromide (25 ml) and potassium carbonate (17.9 g) were added and the stirred mixture heated for another 3 hours. The reaction mixture was filtered and evaporated to afford a solid which on trituration under diethyl ether gave 4-acetamido-2-allyloxyacetophenone (50.77 g), m.p. 108°–110° C.

(ii) A stirred melt of 4-acetamido-2-allyloxyacetophenone (34.95 g) and glyoxylic acid hydrate (13.44 g) was heated at oil bath temperature (105°–110° C.) for 2 hours. The reaction mixture was cooled to 60° C., treated with water (60 ml) and concentrated aqueous ammonia (12 ml) and washed with dichloromethane.

The ammoniacal solution was refluxed for 2 hours with hydrazine hydrate (7.5 ml) to afford 6-(4-acetamido-2-allyloxy)-3[2H]-pyridazinone (23 g) which on recrystallisation from ethanol gave a m.p. of 204°–5° C.

(iii) N-Bromosuccinimide (8.74 g) was added in portions over 20 minutes to a stirred solution of 6-(4-acetamido-2-allyloxy)-3[2H]-pyridazinone (22 g) in anhydrous dimethyl sulphoxide (49 ml) and water (2.45 ml) at a temperature of 10°–15° C. The solution was stirred for 30 minutes at room temperature and diluted with water (200 ml). The crude products were collected, washed with water and dissolved in methanol (70 ml). t-Butylamine (70 ml) was added to this solution and the mixture was refluxed for 16 hours, evaporated under reduced pressure and the residue was heated on a steam bath for one hour with 2N sodium hydroxide solution. The pH was adjusted to 7 with hydrochloric acid and then to 10 with potassium carbonate to give a crude mixture of 6-[4-amino-2-(3-t-butylamino-2-hydroxypropoxy)phenyl]-3[2H]-pyridazinone and 5-bromo analogue thereof. This mixture was dissolved in aqueous sodium hydroxide and hydrogenated at 350 kPa (50 p.s.i.) over 10% Pd/C catalyst. The catalyst was filtered off, and the filtrate adjusted to pH 7 and then to about pH 10 to give the title compound which was crystallised from acetone to give m.p. 198.5°–201.5° C.

The title compound (25 mg), sucrose (40 mg), starch (15 mg), talc (3 mg) and stearic acid (1 mg) are screened, mixed and filled into a hard gelatin capsule.

EXAMPLE 3

4-[2-(3-t-Butylamino-2-hydroxypropoxy)phenyl]-3[2H]-pyridazinone (i) Phenyl magnesium bromide (prepared from bromobenzene (171 g), magnesium (38.8 g) and diethyl ether (1.6 l)) was slowly added to a stirred solution of 4,5-dichloro-3[2H]-pyridazinone (60 g) in tetrahydrofuran (1 l) cooled at water bath temperature. This mixture was stirred at room temperature for 30 minutes and hydrolysed with 20% ammonium chloride solution (800 ml) in the cold. The aqueous layer was extracted with diethyl ether and the combined organic extracts were washed with dilute hydrochloric acid, water, brine, dried (MgSO$_4$) and evaporated under reduced pressure to give 5-chloro-4-phenyl-3[2H]-pyridazinone (55.13 g), m.p. 193°–5° C. on recrystallisation from ethyl acetate.

(ii) The above product (45 g), sodium hydroxide (21.8 g), water (600 ml), dimethylformamide (60 ml) and 10% Palladium on charcoal (1.5 g) were shaken under hydrogen (350 kPa; 50 p.s.i.) until hydrogen uptake was complete. Sodium hydroxide solution was added to dissolve a precipitate and the filtered solution was neutralised to afford 4-phenyl-3[2H]-pyridazinone (35.7 g), m.p. 216.5°–219° C. on recrystallisation from ethanol.

(iii) Powdered 4-phenyl-3[2H]-pyridazinone (32.7) was added over a period of 60 minutes to a stirred mixture of fuming nitric acid (66.6 ml) and concentrated sulphuric acid (6.6 ml) at −10° C. The mixture was stirred at −10° C. for a further 10 minutes and at 0° C. for a further 30 minutes before being poured into ice-water (900 ml) to give a pale yellow mixture of the three isomers of 4-nitrophenyl-3[2H]-pyridazinone (40.65 g), i.e. the 4-(2-nitrophenyl)-, 4-(3-nitrophenyl)- and 4-(4-nitrophenyl)- derivatives.

(iv) The pyridazinones so obtained (20 g), sodium hydroxide (7.73 g), water (600 ml), dimethylformamide (67 ml) and 10% Palladium on charcoal (1 g) were shaken under hydrogen (205 kPa; 30 p.s.i.) until the uptake of hydrogen was complete. This process was repeated on a further amount of the pyridazinone mixture (58.6 g) in batches. Acidification to pH 5-6 of the filtered solutions gave a mixture of 4-(aminophenyl)-3[2H]-pyridazinones (34.46 g). A further quantity of this material (24.41 g) was obtained from the filtrate.

The unpurified product was stirred for 10 minutes with dilute hydrochloric acid (1000 ml), filtered, and evaporated under reduced pressure to afford a residue which was either acetylated as the hydrochloride in water with sodium acetate and acetic anhydride or as the free base with acetic anhydride-pyridine. The resultant mixture of acetamido compounds was digested with chloroform containing methanol to give an impure extract which was purified by column chromatography (silica gel, chloroform-methanol) to give 4-(2-acetamidophenyl)-3[2H]-pyridazinone m.p. 235°-6° C.

Hydrolysis of this material with 18% hydrochloric acid with subsequent evaporation, dissolution in 2N sodium hydroxide and acidification to pH 5-6 afforded 4-(2-aminophenyl)-3[2H]-pyridazinone m.p. 234.5°-236.5° C.

To a stirred mixture of 4-(2-aminophenyl)-3[2H]-pyridazinone (10.64 g), sulphuric acid (7.7 ml) and water (65 ml) at 0° to 5° C. was added dropwise over 20 minutes sodium nitrite (4.16 g) in water (15 ml). After 30 minutes at 5° C., boric acid (5.3 g) and sulphuric acid (7.7 ml) were added, the mixture was warmed to room temperature and subsequently to 70° C. On standing for 18 hours a solid (5.4 g) precipitated. This solid was dissolved in warm water (100 ml) and taken to pH 8 with potassium carbonate to yield a solid (3.32 g). Neutralisation of the acidic reaction mixture yielded further solid (5.32 g). Recrystallisation from cyclohexane of these solids afforded benzofuro[2,3-c]pyridazine m.p. 120°-122° C.

(v) To a stirred solution of benzofuro[2,3-c]pyridazine (5.09 g) in dimethylformamide (40 ml) containing a suspension of sodium hydride (1.68 g, 50% oil) was added dry methanol (1.5 ml). The mixture was heated to 70° C. for 30 minutes and treated with epibromohydrin (10.2 ml) and stirring was continued at room temperature for 150 minutes. The mixture was poured into water (300 ml), taken to pH 10 with sodium hydroxide, extracted into dichloromethane and the organic extract was evaporated under reduced pressure to afford an oil that was purified by column chromatography (silica, chloroformpetrol, chloroform, chloroform-methanol) to afford 4-[2-(2,3-epoxypropoxy)phenyl]-3-methoxypyridazine as an oil. This was heated under reflux for 60 minutes with t-butylamine (20 ml) in methanol (50 ml) and the mixture was allowed to stand overnight. Evaporation under reduced pressure afford an oil which on treat ment with diethyl ether-petrol gave 4-(2-[3-t-butylamino-2-hydroxypropoxy)phenyl]-3-methoxypyridazine, m.p. 109.5°-110.5° C. from cyclohexane.

(vi) The above compound (1.37 g) and 18% hydrochloric acid (82 ml) were heated under reflux for 4 hours. Evaporation under reduced pressure gave a solid which on trituration with diethyl ether afforded 4-(2-[3-t-butylamino-2-hydroxypropoxy)phenyl]-3[2H]-pyridazinone hydrochloride as a quarter hydrate, m.p. 240°-242° C.

The title compound (25 mg), sucrose (40 mg), starch (15 mg), talc (3 mg) and stearic acid (1 mg) are screened, mixed and filled into a hard gelatin capsule.

EXAMPLE 4

6-[2-(3-t-Butylamino-2-hydroxypropoxy)phenyl]-3[2H]-pyridazinone

A stirred solution of 3-[2-(3-t-butylamino-2-hydroxypropoxy)phenyl-6-chloropyridazine (10.0 g, 0.03 mol) in 18% hydrochloric acid (60 ml) was heated under reflux for 8 hours. Potassium carbonate was added to the cold solution to take it to pH 10, and after allowing the mixture to stand for 2 hours the solid was collected by filtration and washed with water to give a crude hydrate (10.35 g). Recrystallisation from ethyl acetate gave 6-[2-(3-t-butylamino-2-hydroxypropoxy)phenyl]-3[2H]-pyridazinone (7.42 g) as a colourless solid, m.p. 161.5°-163.5° C.

The title compound (25 mg), sucrose (40 mg), starch (15 mg), talc (3 mg) and stearic acid (1 mg) are screened, mixed and filled into a hard gelatin capsule.

EXAMPLE 5

6-[2-(2-Hydroxy-3-isopropylaminopropoxy)phenyl]-3[2H]-pyridazinone

A solution of 6-[2-(2-acetoxy-3-N-acetylisopropylaminopropoxy)phenyl]-3[2H]-pyridazinone (3 g) in methanol (75 ml) was heated under reflux with sodium hydroxide (1.58 g) in water (24 ml) for 2 hours. The residue after evaporation was dissolved in water (20 ml) and acetic acid was added dropwise to precipitate the crude product which was recrystallised from ethanol-ether to afford the title compound, m.p. 150.5°-152.5° C. Treatment with ethanolic HCl and crystallisation from ethanol-ether gave as a solid the hydrochloride, m.p. 203°-204° C.

The title compound (25 mg), sucrose (40 mg), starch (15 mg), talc (3 mg) and stearic acid (1 mg) are screened, mixed and filled into a hard gelatin capsule.

EXAMPLE 6

6-[2-(3-t-Butylamino-2-hydroxypropoxy)-4-methoxyphenyl]-3[2H]-pyridazinone

6-[2-(3-t-Butylamino-2-hydroxypropoxy)-4-methoxyphenyl]-3-methoxypyridazine was hydrolysed with hydrochloric acid in a manner similar to that described in Example 3(vi). Addition of an excess of potassium carbonate to the cooled solution afforded the title compound which was recrystallised from ethanol/ether, m.p. 159°-161° C.

*The starting-materials for Examples 4, 5 and 6 are preparable by the methods of U.S. Pat. No. 4,053,601.

The title compound (25 mg), sucrose (40 mg), starch (15 mg), talc (3 mg) and stearic acid (1 mg) are screened, mixed and filled into a hard gelatin capsule.

EXAMPLE 7

5-Methyl-6-[2-(3-t-butylamino-2-hydroxypropoxy)-phenyl]-3[2H]-pyridazinone

5-Methyl-6-[2-(3-t-butylamino-2-hydroxypropoxy)-phenyl]-4,5-dihydro-3[2H]-pyridazinone (preparable from British Patent Specification No. 1488330) (1.3 g) and sodium 3-nitrobenzene sulphonate (0.88 g) were mixed in aqueous sodium hydroxide (0.38 g in 50 ml) and stirred under reflux for 3 hours. The reaction mixture was cooled, neutralised with hydrochloric acid and evaporated under reduced pressure to afford a residue. This was dissolved in water, on standing a solid precipitated which was filtered off (recovered sodium 3-nitrobenzene sulphonate). The filtrate was shaken with chloroform whereupon a white solid precipitated which was collected and dried to afford the title compound (0.4 g).

This was dissolved in dilute hydrochloric acid and the solution was evaporated to dryness. The residue was recrystallised from ethanol/ether to give as a white solid 5-methyl-6-[2-(3-t-butylamino-2-hydroxypropoxy)phenyl]-3[2H]-pyridazinone hydrochloride (0.3 g), m.p. 293°-295° C.

The title compound (25 mg), sucrose (40 mg), starch (15 mg), talc (3 mg) and stearic acid (1 mg) are screened, mixed and filled into a hard gelatin capsule.

EXAMPLE 8

Replacing tertiary-butylamine in Example 1 with isopropylamine gives 5-[2-(2-hydroxy-3-isopropylaminopropoxy)phenyl]-3[2H]-pyridazinone.

EXAMPLE 9

5-(2-Allyloxy-4-methylphenyl)-4,5-dihydro-3[2H]-pyridazinone is reacted with N-bromosuccinimide and subsequently with tertiary-butylamine in a manner similar to that of Example 1 to give 5-[(2-(3-t-butylamino-2-hydroxypropoxy)-4-methyl)phenyl]-3[2H]-pyridazinone.

EXAMPLE 10

5-[2-(3-t-Butylamino-2-hydroxypropoxy)phenyl]-6-methylpyridazinone hydrochloride (i) A solution of the mixture of allyl and methyl esters of 2-allyloxybenzylidenemalonic acid (described in Example 1(i)) in tetrahydrofuran is treated with 1-methylsulphinyl-1-methylthioethane and butyl lithium in hexane at −70° C. to give ethyl 3-(2-allyloxyphenyl)-2-ethoxycarbonyl-4-methyl-4-methylsulphinyl-4-methylthiobutanoate which is subsequently reacted in a manner similar to that described in Example 1(i) to give 4-(2-allyloxyphenyl)-5-ethoxy-5-methyl-2-oxotetrahydrofuran.

(ii) The above tetrahydrofuran is transformed by a sequence of reactions similar to those described in Example 1(ii) and (iii) to give the title compound as a hydrochloride salt.

EXAMPLE 11

5-[2-(3-t-Butylamino-2-hydroxypropoxy)phenyl]-4-methylpyridazinone hydrochloride (i) A solution of ethyl 3-(2-allyloxyphenyl)-4,4-diethoxy-2-ethoxycarbonylbutanoate (described in Example 1(i)), in ether is treated with sodium ethoxide and subsequently with methyl iodide to give ethyl 3-(2-allyloxyphenyl)-4,4-diethoxy-2-ethoxycarbonyl-2-methylbutanoate, which is subsequently reacted in a manner similar to that described in Example 1(i) to give 4-(2-allyloxyphenyl)-5-ethoxy-3-methyl-2-oxotetrahydrofuran.

(ii) The above tetrahydrofuran is transformed by a sequence of reactions similar to those described in Example 1(ii) and (iii) to give the title compound as a hydrochloride salt.

What is claimed is:

1. A compound of the formula (III):

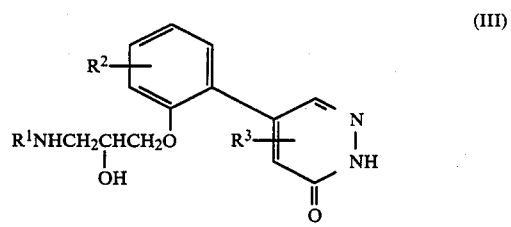

or a pharmaceutically acceptable salt thereof wherein $R^1$ is isopropyl or tertiary-butyl, $R^2$ is hydrogen, $C_{1-4}$alkyl, $C_{1-4}$alkoxy, hydroxy, or amino; and $R^3$ is hydrogen.

2. A compound of the formula (V):

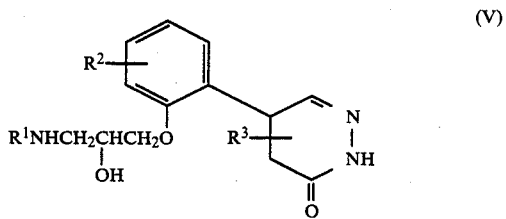

wherein $R^1$ is isopropyl or tertiary-butyl, $R^2$ is hydrogen, $C_{1-4}$alkyl, $C_{1-4}$alkoxy, hydroxy, or amino and $R^3$ is hydrogen.

3. A compound of the formula (VI):

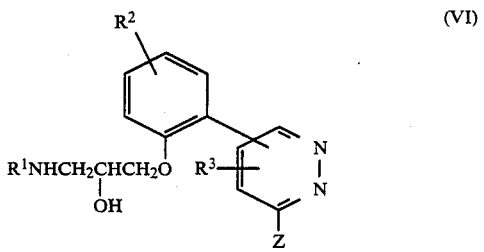

wherein $R^1$ is isopropyl or tertiary-butyl; $R^2$ is hydrogen, $C_{1-4}$alkyl, $C_{1-4}$alkoxy, hydroxy, or amino and $R^3$ is hydrogen and Z is $C_{1-6}$alkoxy, allyloxy or benzyloxy.

4. A compound according to claim 1 wherein $R^1$ is a tertiary-butyl group.

5. A compound according to claim 1 wherein $R^2$ is hydrogen or methyl.

6. A compound according to claim 4 wherein $R^3$ is hydrogen.

7. A compound according to claim 1 which is 5-[2-(3-t-butylamino-2-hydroxypropoxy)phenyl]-3[2H]-pyridazinone or a pharmaceutically acceptable salt thereof.

8. A compound according to claim 1 which is 5-[2-(2-hydroxy-3-isopropylaminopropoxy)phenyl]-3[2H]-pyridazinone or a pharmaceutically acceptable salt thereof.

9. A compound according to claim 1 which is 5-[2-(3-t-butylamino-2-hydroxypropoxy)phenyl]-3-[2H]-pyridazinone hydrochloride.

10. A compound according to any one of claims 2 to 3 wherein $R^2$ and $R^3$ are both hydrogen.

* * * * *